United States Patent

Hough et al.

[11] Patent Number: 5,604,181
[45] Date of Patent: Feb. 18, 1997

[54] PYRIMIDINE DERIVATIVES HERBICIDES

[75] Inventors: Thomas L. Hough; Peter S. Gates, both of Cambridge, England

[73] Assignee: Agrevo UK Limited, England

[21] Appl. No.: 397,123

[22] PCT Filed: Aug. 27, 1993

[86] PCT No.: PCT/EP93/02339

§ 371 Date: Mar. 8, 1995

§ 102(e) Date: Mar. 8, 1995

[87] PCT Pub. No.: WO94/05644

PCT Pub. Date: Mar. 17, 1994

[30] Foreign Application Priority Data

Sep. 9, 1992 [GB] United Kingdom .................. 9219115

[51] Int. Cl.[6] ...................... C07D 239/32; C07D 239/52; A01N 43/54

[52] U.S. Cl. ........................... 504/242; 504/196; 504/197; 504/239; 504/240; 504/241; 504/243; 544/122; 544/123; 544/319; 544/326; 544/327; 544/328; 544/329; 544/333; 544/334; 544/335; 544/242; 544/243; 544/244

[58] Field of Search ..................... 504/196, 197, 504/239, 240, 243; 544/122, 326, 329, 335, 244

[56] References Cited

FOREIGN PATENT DOCUMENTS

| 0410590 | 1/1991 | European Pat. Off. . |
| 0422751 | 4/1991 | European Pat. Off. . |
| 9209584 | 6/1992 | WIPO . |

OTHER PUBLICATIONS

Vakhatova et al., Chemical Abstracts, vol. 92, enty 128865c (1990).
Lapachev et al., Chemical Abstracts, vol. 101, entry 238865C (1980).
Vakhatova, G. M., et al., "S–Trazine Derivatives 1", Chemical Abstracts, vol. 92, No. 15, 1980, Abstract No. 128865c, p. 698, column 2.

*Primary Examiner*—John M. Ford
*Attorney, Agent, or Firm*—Ostrolenk, Faber, Gerb & Soffen, LLP

[57] ABSTRACT

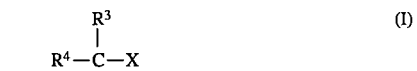

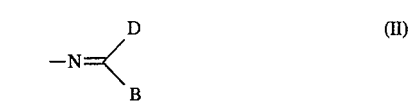

Herbicidal compounds of formula (I) and salts thereof, where A is $-N=$ or $-CH=$; X is $-OH$, $-OR^{10}$, $-SH$, $-SR^{10}$, $-SCN$, $NH_2$, $-NHacyl$, $-CH_2OH$, $-CH_2OR^9$ or $-CN$; $R^1$ and $R^2$, which may be the same or different, each represent alkyl, alkoxy, haloalkyl, haloalkoxy, halo, alkylamino or dialkylamino; $R^3$ is $-CN$, $-COOR^5$, $-CONR^6R^7$, $-CSNH_2$, $-CHO$, $-CH=Z$, $-CH(O-alkyl)_2$, $-CH_2OH$, $-CH_2OR^9$, $-COSR^{4a}$, $-CS_2R^{4a}$, or a substituted or unsubstituted 5- or 6-membered heterocyclic group linked via a ring carbon atom which is between two ring heteroatoms; $R^4$ and $R^{4a}$, which may be the same or different, are each H, or a substituted or unsubstituted alkyl, alkenyl, alkynyl, cycloalkyl, aryl, aralkyl or heteroaryl group; $R^5$ is H, or a substituted or unsubstituted alkyl, alkenyl, alkynyl, cycoalkyl, aryl, aralkyl or heteroaryl group, or a group of formula (II) where B and D are each alkyl, or together with the carbon atom to which they are attached form a 5-, 6- or 7-membered carbocyclic or heterocyclic ring; $R^6$ is a group as defined for $R^{4a}$, and $R^7$ is a group as defined for $R^{4a}$ or is $-SO_2R^8$, $-OH$, $-CN$, $-OR^{10}$, $-NH_2$ or $-NHR^{10}$; or $R^6$ and $R^7$ together form a ring; $R^8$ is a substituted or unsubstituted alkyl alkenyl, alkynyl, cycloalkyl, aralkyl, aryl or heteroaryl group, or a group $-NR^{4b}R^{4c}$ where $R^{4b}$ and $R^{4c}$, which may be the same or different, are each a group as defined for $R^{4a}$, or together form a ring; $R^9$ is a substituted or unsubstituted alkyl, alkenyl, alkynyl, cycloalkyl, aralkyl or acyl group; $R^{10}$ is a substituted or unsubstituted alkyl, alkenyl, alkynyl, cycloalkyl, aryl, aralkyl, heteroaryl or acyl group; Z is $=NOR^{4a}$ or $=N-NR^{4d}R^{12}$, where $R^{4d}$ is a group as defined for $R^{4a}$, and $R^1$ is a group as defined for $R^{4a}$ or is a substituted or unsubstituted acyl group, or $R^{4d}$ and $R^{12}$ together form a ring; with the proviso that, when $R^4$ is ortho-substituted phenyl or naphthyl, any ortho-substituent thereon is halogen, $-NO_2$, $-OH$, $-OR^{10}$, $-SH$, $-SR^8$, $-SOR^8$, $-SO_2R^8$, $-NH_2$, $-NR^6R^{10}$, aryl or heteroaryl.

21 Claims, No Drawings

PYRIMIDINE DERIVATIVES HERBICIDES

This application was filed pursuant to 35 U.S.C. §371 based on PCT/EP93/02339, filed Aug. 27, 1993.

1. Field of the Invention

This invention concerns new pyrimidine and triazine derivatives having herbicidal activity, processes for their preparation and herbicidal compositions containing them.

2. Prior Art

Certain pyrimidinyl and triazinyl acetic acid derivatives having herbicidal activity have previously been described, for example in our earlier patent applications EP 410590, WO 92/1677 and WO 92/16511, and in EP 461079.

DESCRIPTION

In one aspect, this invention provides the compounds of the formula:

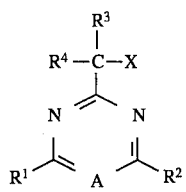

and salts thereof, where:

A is —N= or —CH=;

X is —OH, —OR$^{10}$, —SH, —SR$^{10}$, —SCN, NH$_2$, —NHacyl, —CH$_2$OH, or —CN;

R$^1$ and R$^2$, which may be the same or different, each represent alkyl, alkoxy, haloalkyl, haloalkoxy, halo, alkylamino or dialkylamino;

R$^3$ is —CN, —COOR$^5$, —CONR$^6$R$^7$, —CSNH$_2$, —CHO —CH=Z, —CH(Oalkyl)$_2$, —CH$_2$OH, —COSR$^{4a}$, —CS$_2$R$^{4a}$, or a substituted or unsubstituted 5- or 6-membered heterocyclic group linked via a ring carbon atom which is between two ring heteroatoms;

R$^4$ and R$^{4a}$, which may be the same or different, are each H, or a substituted or unsubstituted alkyl, alkenyl, alkynyl, cycloalkyl, phenyl, phenylalkyl or heteroaryl group;

R$^5$ is H, or a substituted or unsubstituted alkyl, alkenyl, alkynyl, cycloalkyl, phenyl, phenylalkyl or heteroaryl group, or a group of the formula:

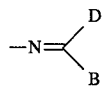

where B and D are each alkyl, or together with the carbon atom to which they are attached form a 5-, 6- or 7-membered carbocyclic or heterocyclic ring;

R$^6$ is a group as defined for R$^{4a}$, and R$^7$ is a group as defined for R$^{4a}$ or is —SO$_2$R$^8$, —OH, —CN, —OR$^{10}$, —NH$_2$ or —NHR$^{10}$; or R$^6$ and R$^7$ together with the nitrogen atom to which they are attached form a morpholino group;

R$^8$ is a substituted or unsubstituted alkyl, alkenyl, alkynyl, cycloalkyl, aralkyl, phenyl or heteroaryl group, or a group —NR$^{4b}$R$^{4c}$ where R$^{4b}$ and R$^{4c}$, which may be the same or different, are each a group as defined for R$^{4a}$, or together form a ring;

R$^{10}$ is a substituted or unsubstituted alkyl, alkenyl, alkynyl, cycloalkyl, phenyl, phenylalkyl, heteroaryl or acyl group;

Z is =NOR$^{4a}$ or =N—NR$^{4d}$R$^{12}$, where R$^{4d}$ is a group as defined for R$^{4a}$, and R$^{12}$ is a group as defined for R$^{4a}$ or is a substituted or unsubstituted acyl group, or R$^{4d}$ and R$^{12}$ together form a ring;

any alkyl group present in the molecule, unless otherwise defined, is of 1 to 8 carbon atoms and, if substituted, is substituted by one or more halogen atoms, alkoxy groups of 1 to 4 carbon atoms, hydroxy, nitro, mercapto, amino, substituted amino, cyano, acyl, aryl or heteroaryl groups, or groups of the formula —SR$^8$ or —SOR$^8$, where R$^8$ represents a substituted or unsubstituted alkyl, alkenyl, alkynyl, cycloalkyl, aralkyl, acyl or amino group;

any alkenyl or alkynyl group present in the molecule is of 2 to 6 carbon atoms and, if substituted, is substituted by halogen;

any cycloalkyl group present in the molecule is of 3 to 7 carbon atoms;

any phenyl group present in the molecule, if substituted, is substituted by one or more halogen atoms, optionally substituted alkyl or alkoxy groups of 1 to 4 carbon atoms, hydroxy, nitro, mercapto, amino, substituted amino, cyano, acyl, aryl or heteroaryl groups, or groups of the formula —SR$^8$ or —SOR$^8$;

any heteroaryl group present in the molecule is an aromatic heterocyclic group which, when mononuclear, is of 5 or 6 ring atoms and contains at least one atom of nitrogen, oxygen or sulfur, when polynuclear is a benzoheterocyclic group, and which, if substituted, is substituted by one or more halogen atoms, nitro groups, amino, alkylamino, dialkylamino or acylamino groups, cyano groups, or alkyl or alkoxy groups of 1 to 4 carbon atoms; and any acyl group present in the molecule is a residue of a carboxylic, sulfonic or phosphorus-containing acid;

with the exception of the compound where R$^1$ and R$^2$ are both methoxy, X is —NH$_2$, R$^3$ is —CONH$_2$ and R$^4$ is H;

and with the proviso that, when R$^4$ is ortho-substituted phenyl or naphthyl, any ortho-substituent thereon is halogen, —NO$_2$, —OH, —OR$^{10}$, —SH, —SR$^8$, —SOR$^8$, —SO$_2$R$^8$, —NH$_2$, —NR$^6$R$^{10}$, aryl or heteroaryl.

Any alkyl group present in the molecule is preferably of 1 to 6 carbon atoms, and particularly of 1 to 4 carbon atoms. Specific preferred unsubstituted alkyl or alkyl-containing groups include methyl, ethyl, n-propyl, isopropyl, n-butyl, t-butyl, methoxy, ethoxy and n-propoxy.

When any alkyl group in the molecule is substituted by halogen this may for example be fluorine, chlorine or bromine, and when substituted by alkoxy, this may be methoxy or ethoxy. Specific preferred substituted alkyl-containing groups include chloromethyl, bromomethyl, dichloromethyl, trifluoromethyl, difluoromethoxy, methoxyethyl and ethoxyethyl.

Any alkenyl or alkynyl group present in the molecule is preferably allyl, vinyl or propargyl. Any such alkenyl or alkynyl group is preferably unsubstituted.

Any cycloalkyl group present in the molecule is preferably cyclopentyl or cyclohexyl. It is preferably unsubstituted.

Any halogen atom present in the molecule is preferably fluorine, chlorine or bromine.

Any phenylalkyl group present in the molecule is preferably a substituted or unsubstituted benzyl group.

Halogen substituents on any phenyl group present in the molecule are preferably fluorine, chlorine or bromine. Alkyl or alkoxy substituents on any phenyl group are preferably optionally substituted alkyl or alkoxy groups of 1 to 4 carbon atoms (eg methyl, ethyl, methoxy or ethoxy). Substituted amino substituents on any phenyl group are preferably alkylamino, dialkylamino or acylamino groups especially where the alkyl moieties have from 1 to 4 carbon atoms.

Preferred mononuclear heterocyclic groups are furyl, thienyl, pyrrolyl, oxazolyl, thiazolyl, imidazolyl, pyrazolyl, pyridinyl, pyrazinyl and thiadiazolyl.

Preferred polynuclear heterocyclic groups are indolyl, benzofuranyl, benzimidazolyl and quinolinyl.

Halogen substituents on any heterocyclic groups in the molecule are preferably chlorine, fluorine or bromine atoms. Alkylamino, dialkylamino or acylamino substituents on any heterocyclic groups are preferably those where the alkyl moieties are of 1 to 4 carbon atoms, and alkyl or alkoxy substituents on any heterocyclic groups are preferably of 1 to 4 carbon atoms, eg methyl, ethyl, methoxy or ethoxy.

Examples of any acyl groups present in the molecule are alkanoyl, alkenoyl, alkynoyl, cycloalkanoyl, aralkanoyl, aroyl, carbamoyl, thiocarbamoyl, alkoxycarbonyl, sulfonyl, sulfamoyl and phosphonyl groups, in which any alkyl, alkenyl, alkynyl or aryl group may be substituted or unsubstituted.

The salts of the compounds of formula I are preferably those formed with alkali-metals (eg lithium, sodium or potassium), ammonium salts, or those formed with organic amines such as cyclohexylamine or piperidine.

A preferably represents —CH=.

X is preferably —OH or —OR$^{10}$, particularly where R$^{10}$ represents alkyl of 1 to 4 carbon atoms, eg methyl, or alkanoyl of 2 to 5 carbon atoms, eg acetyl.

R$^1$ is preferably chloro, methyl, methoxy, difluoromethoxy or ethoxy, especially methoxy.

R$^2$ is preferably methyl, methoxy or difluoromethoxy, especially methoxy.

R$^3$ is preferably a group —COOR$^5$ (where R$^5$ is optionally substituted alkyl of 1 to 4 carbon atoms, eg methyl or ethyl), or —CONR$^6$R$^7$ where R$^6$ is hydrogen and R$^7$ is a group —SO$_2$R$^8$ (particularly where R$^8$ is alkyl of 1 to 4 carbon atoms, eg methyl, ethyl or isopropyl, cyclopropyl or dimethylamino), or where R$^6$ and R$^7$ together with the nitrogen atom to which they are attached form a morpholino ring. Examples of other groups which R$^3$ may advantageously represent include —CH=Z (where Z is NNH-COCH$_3$ or NOCH$_3$), —CH(OCH$_3$)$_2$, or a dioxolan, thiazolyl or oxadiazolinone ring.

R$^4$, R$^{4a}$, R$^{4b}$, R$^{4c}$ and R$^{4d}$ are independently perferably an unsubstituted alkyl group, especially isopropyl or secbutyl, or an aryl group, especially phenyl or substituted phenyl, eg halo-substituted phenyl, particularly 3-fluorophenyl.

R$^5$ is preferably optionally-substituted alkyl of 1 to 4 carbon atoms, especially methyl or ethyl.

The compounds of formula I may possess one or more asymmetric centres. This invention extends to all separate stereoisomers which may exist, as well as to mixtures thereof whether racemic or not.

Specific preferred compounds according to the invention are those of the Examples provided hereinafter.

The compounds of formula I where R$^3$ is —CN, —CO$_2$R$^5$ or —CONR$^6$R$^7$ may be prepared by a process in which a compound of the formula:

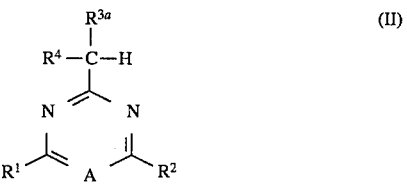

where A, R$^1$, R$^2$ and R$^4$ are as defined above, and R$^{3a}$ is —CN, —CO$_2$R$^5$ or —CONR$^6$R$^7$ (where R$^5$, R$^6$ and R$^7$ are as defined above) is subjected to the action of an appropriate electrophile in the presence of a strong base.

Suitable electrophiles include p-toluenesulfonyl cyanide, camphorsulfonyloxaziridine, O-diphenyl-phosphinylhydroxylamine, methyl methanethiolsulfinate and formaldehyde.

The strong base employed may, for example, be butyllithium or lithium diisopropylamide, and the reaction is desirably effected at reduced temperature, eg at –78° C., and in a suitable solvent, eg tetrahydrofuran.

Compounds of formula II and processes for their preparation are described in European Patent specification no 410590. Any compounds of formula II not described therein may be made by analogous processes.

Compounds of formula I where X is —OH or OR$^{10}$, especially those where R$^3$ is —CONR$^6$SO$_2$R$^8$, may also be prepared by a process in which a compound of the formula:

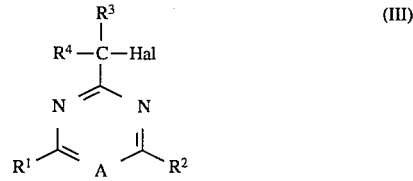

where R$^1$, R$^2$, R$^3$ and R$^4$ are as defined hereinbefore, and Hal is chlorine, bromine or iodine, is subjected to the action of an anion-forming base to give the desired compound.

To give the compounds of formula I where X is —OH, the base is preferably an aqueous alkali-metal hydroxide, carbonate or bicarbonate. To give the compounds of formula I where X is —OR$^{10}$, the base is preferably a compound M—OR$^{10}$, where M is an alkali-metal and the reaction is desirably effected in a suitable solvent, eg methanol.

Compounds of formula III and processes for their preparation are described in WO 92/1677 and WO 92/16511. Any compounds of formula III not described therein may be made by processes analogous to those described.

The compounds of formula I where R$^3$ is other than —CN, —COOR$^5$ or —CONR$^6$R$^7$ as defined hereinbefore, may be prepared from such compounds by conventional techniques well known to those skilled in the art.

In particular, the compounds of formula I where R$^3$ is carboxy may be prepared from the corresponding esters by hydrolysis, and many further conversions of the acid or ester function can be effected in known ways.

For example, the compounds of formula I where R$^3$ is a group —COOR$^5$ may be reduced, eg by means of diisobutylaluminium hydride, to the corresponding compounds where R$^3$ is a group —CHO (using one molar proportion of the hydride) or —CH$_2$OH (using two molar proportions of the hydride). The reductions are conveniently effected in a suitable solvent medium, eg tetrahydrofuran, and with cooling, eg to 5° C.

The compounds of formula I where R$^3$ is —CH$_2$OH can be acylated or etherified to give the corresponding compounds where R$^3$ is a group —CH$_2$OR$^9$.

The compounds of formula I where R$^3$ is —CHO can be converted by known techniques to the corresponding hydrazones (eg by reaction with a compound of formula H$_2$N—

$NR^{4d}R^{12}$ in a suitable solvent medium, eg an alcohol), oximes (eg by reaction with a compound of formula $H_2NOR^{4a}$ in a suitable solvent medium, eg an alcohol), ketals, 1,3-dioxolanes, 1,3-dithiolanes, 1,3-dioxanes, 1,3-dithianes or imidazolidines (eg by heating in the presence of an acid catalyst with a compound of formula RQH or $HQ-(CH_2)_{2-3}-QH$ where Q is O, S or NH).

In addition, the compounds of formula I where $R^3$ is carboxy or a salt may be converted to the corresponding compounds in which $R^3$ is a group $-CONHSO_2R^8$ or a group $-COSR^{4a}$ by a two-stage process in which the acid or salt is first reacted with oxalyl chloride to give the corresponding acyl chloride, and this is then reacted either with a compound of the formula $NaNHSO_2R^8$, or in the presence of a base with a compound of the formula $R^{4a}SH$, to give the desired compound.

In turn, the compounds of formula I where $R^3$ is a group $-COSR^{4a}$ and X is a protected $-OH$, $-SH$, $-NH_2$ or $-CH_2OH$ group, may be reacted with Lawesson's reagent to give the corresponding compounds where $R^3$ is a group $-CS_2R^{4a}$, the protection if desired being subsequently removed.

The compounds of formula I where X is $-CN$ and $R^3$ is $-CS_2R^{4a}$ may be prepared from the corresponding compounds where $R^3$ is H by reaction thereof with a compound of the formula $R^{4a}SC(=S)Cl$ in the presence of a strong base, eg n-butyllithium.

The compounds of formula I where $R^3$ is $-CN$ can be converted by known techniques into the corresponding thioamides where $R^3$ is $-CSNH_2$ (eg by reaction with hydrogen sulfide in a suitable base such as pyridine).

The compounds of formula I where $R^3$ is a heterocycle may be prepared by ring closure procedures well known per se carried out on the corresponding compounds of formula I where $R^3$ is $-CN$, $-CSNH_2$ or $-CONR^6R^7$. For example, the compounds of formula I where $R^3$ is $-CN$ may be converted by the action of ammonia into the corresponding compounds where $R^3$ represents $-C(=NH)NH_2$ which may be further reacted with α-haloketones, α-haloacid chlorides or β-diketones to give, respectively, the corresponding imidazoles, imidazolones and pyrimidines. Similarly, ring closure reactions may be performed on the compounds of formula I where $R^3$ represents $-CSNH_2$ for example by reaction thereof with dibromoethane, or on the compounds of formula I where $R^3$ is $-CONR^6R^7$ for example by reaction thereof with an acid chloride or anhydride.

The salts of the compounds of formula I may be prepared by reaction of the corresponding unsalified compound of formula I with an appropriate salt-forming base by methods known per se.

The compounds of formula I and the salts thereof are herbicidally-active against a wide range of broadleaf and grass weeds, but are comparatively safe to certain crop species. They may thus be of use as herbicides, and especially as selective herbicides, particularly in cereals, eg maize, wheat or rice, in beet crops, eg sugar beet, in soybeans or in cotton.

In another aspect, therefore, this invention provides a herbicidal composition which comprises one or more compounds of formula I or salts thereof in association with a suitable carrier and/or surface active agent.

The compositions of the invention usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent,e.g. xanthan gum.

The carrier may alternatively be a water immiscible organic solvent, e.g. a hydrocarbon which boils within the range 130°–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxyethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulfonates and solid fertilizers. The carrier can be natural or synthetic or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulfates such as sodium dodecyl sulfate, ethoxylated fatty alcohol sulfates, ethoxylated alkylphenol sulfates, lignin sulfates, petroleum sulfonates, alkylaryl sulfonates such as alkyl-benzene sulfonates or lower alkylnaphthalene sulfonates, salts of sulfonated naphthaleneformaldehyde condensates, salts of sulfonated phenolformaldehyde condensates, or more complex sulfonates such as the amide sulfonates, e.g. the sulfonated condensation product of oleic acid and N-methyl taurine or the dialkyl sulfosuccinates e.g. the sodium sulfonate of dioctyl succinate.

The surface active agents may also comprise non-ionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyt-5-decyn-4,7-diol, or ethoxylated acetylenic glycols.

The surface active agents may also comprise cationic agents, for example alkyl- and/or aryl-substituted quaternary ammonium compounds such as cetyl trimethyl-ammonium bromide, or ethoxylated tertiary fatty amines.

Preferred surface active agents include ethoxylated fatty alcohol sulfates, lignin sulfonates, alkyl-aryl sulfonates,salts of sulfonated naphthaleneformaldehyde condensates, salts of sulfonated phenolformaldehyde condensates, sodium oleoyl N-methyltauride, dialkyl sulfosuccinates, alkyl phenol ethoxylates, and fatty alkyl ethoxylates.

The present active compounds may be admixed with another pesticide, eg a herbicide, fungicide or insecticide, or a plant growth regulator, particularly another herbicide. Suitable further herbicides include trietazine, linuron, MCPA, dichlorprop, isoxaben, diflufenican, metolachlor, fluometuron, oxyfluorfen, fomesafen, bentazone, prometryne, norflurazon, chlomazone, EPTC, imazaquin, and especially isoproturon, methabenzthiazuron, trifluralin, ioxynil, bromoxynil, benazolin, mecoprop, fluroxypyr, alachlor, acifluorfen, lactofen, metribuzin, pendimethalin, ethofumesate, benfuresate, phenmedipham, benzophenap, butachlor, chlomethoxyfen, dimepiperate, mefenacet, molinate, naproanilide, oxadiazon, piperophos, prometryne, pyrazoxyfen, pyrazosulfuron-ethyl, bensulfuron, simetryne, pyrazolate, pretilachlor, thiobencarb and pyributicarb.

The present compounds may be applied to plants, the soil, land or aquatic areas, and particularly to a locus at which a crop is growing. The compounds are active both pre- and post-emergence, and may be employed at rates of from 1 g to 2 kg/ha.

EXAMPLES

The invention is illustrated by the following Examples, in which Me=methyl, Et=ethyl, Pr=propyl, and Ph=phenyl.

Example 1

Methyl 2-cyano-2-phenyl-2-(4,6-dimethoxypyrimidin-2-yl)acetate

Lithium diisopropylamide was prepared by adding a solution of n-butyllithium (4 ml, 2.5M in hexane) slowly by syringe into a solution of diisopropylamine (1.01 g) in dry tetrahydrofuran (20 ml) at −65° C. under nitrogen. After stirring at −65° C. for 20 minutes, a solution of methyl 2-phenyl-2-(4,6-dimethoxypyrimidin-2-yl)acetate (2.88 g) in dry tetrahydrofuran (10 ml) was added by syringe. The solution was again stirred for 20 minutes, after which p-toluenesulfonyl cyanide (1.81 g) was added in one portion. The mixture was allowed to warm to room temperature, and was stirred for 3 hours. It was then poured into saturated ammonium chloride solution. The product was extracted with diethyl ether (2×50 ml), dried, evaporated to dryness under vacuum, and flash chromatographed on silica gel, eluting with ethyl acetate/60°–80° petroleum ether (1:4), to give 0.9 g of the desired product as a white solid, mp 91°–93° C.

Examples 2–7

The following compounds of formula I in which A is —CH=, $R^1$ and $R^2$ are both methoxy, and $R^3$ is —COOR$^5$ were prepared by methods analogous to that of Example 1:

| Ex | $R^4$ | $R^5$ | X | M Pt (°C.) |
|---|---|---|---|---|
| 2 | Ph | Me | OH | Oil |
| 3 | Ph | Me | NH$_2$ | Oil |
| 4 | Ph | Me | SMe | 97–99 |
| 5 | Ph | Me | CH$_2$OH | Oil |
| 6 | i-Pr | Et | NH$_2$ | Oil |
| 7 | i-Pr | Et | OH | 90–91. |

The electrophiles used in the above examples were:
  Examples 2 and 7: camphorsulfonyloxaziridine
  Examples 3 and 6: O-diphenylphosphinylhydroxylamine
  Example 4: methyl methanethiolsulfinate
  Example 5: formaldehyde.

Example 8

Methyl 2-methoxy-2-phenyl-2-(4,6-dimethoxypyrimidin-2-yl)acetate

A solution of methyl 2-hydroxy-2-phenyl-2-(4,6-dimethoxypyrimidin-2-yl) acetate (0.608 g) in dry acetonitrile (10 ml) was stirred at room temperature with silver carbonate (1.1 g), silver fluoroborate (0.39 g) and methyl iodide (0.568 g) for 24 hours, and was allowed to stand for 7 days. The mixture was then filtered, and the filtrate evaporated to dryness under vacuum. The residue was shaken with a mixture of 2N sodium carbonate solution (20 ml) and dichloromethane (20 ml) for several minutes. It was then again filtered, and the organic solution was dried and evaporated to dryness, the residue being flash chromatographed on silica gel, eluting with ethyl acetate/60°–80° petroleum ether (1:4), to give 0.155 g of the desired product as a white solid, mp 72°–76° C.

Example 9

Ethyl 2-[3-(2-chlorophenyl)ureido]-2-(4,6-dimethoxypyrimidin-2-yl)-3-methylbutanoate A solution of ethyl 2-amino-3-methyl-2-(4,6-dimethoxypyrimidin-2-yl)butanoate (0.556 g) and 2-chlorophenylisocyanate (0.306 g) in ethyl acetate (30 ml) was refluxed for 5 hours, evaporated to dryness, and flash chromatographed on silica gel, eluting with ethyl acetate/60°–80° petroleum ether (1:2). The residual gum was triturated with 60°–80° petroleum ether, to give 0.76 g of the desired product as a white solid, mp 84°–87° C.

Example 10

Ethyl 3-methyl-2-(4,6-dimethoxypyrimidin-2-yl)-2-(2-chlorobenzamido)butanoate

2-Chlorobenzoyl chloride (0.35 g) in ethyl acetate (3 ml) was added to a stirred solution of ethyl 2-amino-3-methyl-2-(4,6-dimethoxypyrimidin-2-yl)butanoate (0.566 g) and ethyl diisopropylamine (0.258 g) in ethyl acetate (15 ml). The mixture was stirred at room temperature for 2 hours, filtered, and the filtrate was washed with water, dried and evaporated to dryness under vacuum. The residual solid was triturated with 60°–80° petroleum ether to give 0.4 g of the desired product as a white solid, mp 94°–95° C.

Examples 11–15

The following compounds of formula I in which A is —CH= and $R^1$ and $R^2$ are both methoxy, were prepared by methods analogous to that of Examples 9–10:

| Ex | $R^4$ | $R^5$ | X | M Pt (°C.) |
|---|---|---|---|---|
| 11 | i-Pr | Et | NHCONHCOOEt | 148–150 |
| 12 | i-Pr | Et | NHSO$_2$CF$_3$ | 83–85 |
| 13 | i-Pr | Et | NHCOMe | 92–94 |
| 14 | i-Pr | Et | NHCOCH=CH$_2$ | 79–81 |
| 15 | i-Pr | Et | NHCOOMe | Oil |

Example 16

Ethyl 2-(4,6-dimethoxypyrimidin-2-yl)-2-thiocyanato-3-methylbutanoate

Potassium thiocyanate (0.97 g) was added to a stirred solution of ethyl 2-(4,6-dimethoxypyrimidin-2-yl)-3-methyl butanoate (2.68 g) in acetic acid (10 ml). After all the potassium thiocyanate had dissolved, the stirred solution was treated dropwise over 30 minutes with a solution of bromine (1.6 g) in acetic acid (5 ml). The resulting solution was stirred for 2 hours at room temperature, and was then poured into water (150 ml). The aqueous solution was extracted with dichloromethane, and the dichloromethane layer was washed with 10% aqueous sodium carbonate solution, dried, evaporated to dryness, and flash chromatographed on silica gel, eluting with ethyl acetate/6°–80° C. petroleum ether (1:7), to give 1.0 g of the desired product as a gum.

Example 17

Ethyl 2-(4,6-dimethoxypyrimidin-2-yl) -2-mercapto-3-methylbutanoate

A mixture of the product of Example 16 (0.8 g), trifluoroacetic acid (1 ml) and dichloromethane (10 ml) was stirred at room temperature for 24 hours, and was then washed with water and aqueous sodium bicarbonate. The organic layer was dried, evaporated to dryness under vacuum, and flash chromatographed on silica gel, eluting with ethyl acetate/ 60°–80° petroleum ether, to give 0.25 g of the desired product which partly solidified.

Examples 18–19

The following compounds of formula I in which A is —CH= and $R^1$ and $R^2$ are both methoxy, were prepared by methods analogous to that of Examples 16 and 17:

| Ex | $R^4$ | $R^5$ | X | M Pt (°C.) |
|---|---|---|---|---|
| 18 | Ph | Me | SCN | 99–102 |
| 19 | Ph | Me | SH | 157–160 |

Example 20

2-(4,6-Dimethoxypyrimidin-2-yl)-2-hydroxy-N-methanesulfonyl-2-phenylacetamide (a) Lithium 2-chloro-2-(4,6-dimethoxypyrimidin-2-yl)-2phenyl acetate n-Butyllithium (19.6 ml of 2.5M solution in hexane) was added portionwise to diisopropylamine (5.0 g) in dry tetrahydrofuran (70 ml) with stirring under nitrogen at –78° C. Stirring was continued for 20 minutes. The solution of lithium diisopropylamide was warmed to ice-bath temperature and added dropwise (by syringe) with stirring to 2-(α-chlorobenzyl)-4,6-dimethoxypyrimidine (13.0 g) in dry tetrahydrofuran (100 ml) with stirring under nitrogen at –78° C. over 15 minutes. Stirring was continued for 25 minutes. The reaction mixture was then added all at once to excess solid carbon dioxide and stirred, as much as possible, for 1½ hours. After warming to room temperature, the solution was evaporated under vacuum at less than 50° C. The residue was treated with ether (100 ml) and the solid lithium salt filtered off, washed with ether, and dried without heat to give 18.4 g of the desired product (contaminated with diisopropylamine carbonate).

(b) 2-chloro-2-(4,6-dimethoxypyrimidin-2-yl)-2phenylacetyl chloride

Dimethyl formamide (1.65 ml) was added with stirring and ice-bath cooling (5° C.) to oxalyl chloride (33 ml) in dry dichloromethane (200 ml). The product from Stage (a) was added portionwise at 5°–10° C. over 5 minutes. Stirring was continued for 10 minutes at 5° C., then for 1½ hours at room temperature and 15 minutes at reflux. All volatiles were distilled off at <50° C. under partial/full vacuum; and the residue was treated with dry ether (300 ml). The precipitated solid was filtered off and washed with ether. The ether solution was then evaporated under vacuum to give 12.8 g of the desired product as a brown oil. NMR showed this to be approximately 85% pure.

(c) 2-chloro-2-(4,6 dimethoxypyrimidin-2-yl)-N-methanesulfonyl-2-phenylacetamide The product from Stage (b) (3.1 g) in dry tetrahydrofuran (10 ml) was added dropwise to stirred, cooled (5° C.) methanesulfonamide sodium salt (2.8 g) in dry tetrahydrofuran (25 ml). Stirring was continued until most solid had dissolved (2 hours) and the reaction mixture was allowed to stand at room temperature overnight. The solvent was then evaporated off under vacuum and the residue was treated with ether. The precipitated solid was taken up in aqueous potassium bicarbonate, the ether solution extracted again with bicarbonate and then with water. The combined aqueous phases were washed with ether, fresh ether was then added and the whole was acidified to pH=1 with hydrochloric acid as quickly as possible with stirring. The ether solution was separated, and the aqueous phase was extracted twice more. The combined ether solutions were washed with water (5 times), dried over magnesium sulfate and evaporated under vacuum to give 2.3 g of the desired product. Washing with a small volume of diisopropyl ether gave 1.95 g of pure product as a viscous liquid.

(d) 2-(4,6-Dimethoxypyrimidin-2-yl)-2-hydroxy N-methanesulfonyl-2-phenylacetamide 2-Chloro-2-(4,6-dimethoxypyrimidin-2-yl)-N-methanesulfonyl-2-phenylacetamide (0.5 g) was stirred at room temperature with potassium bicarbonate (0.2 g) in water (10 ml) for 2 hours, by which time all was in solution. After standing for 3 days, the solution was washed with ether (twice) and acidified with hydrochloric acid. Ether extraction (3 times), washing with water (twice), drying over magnesium sulfate and evaporation under vacuum gave 0.45 g of the desired product as a yellow glass. This glass slowly crystallised to a solid, mp 94°–6° C.

Examples 21–27

The following compounds of formula I where A is —CH=, $R^1$ and $R^2$ are both methoxy, X is —OH, and $R^3$ is —CONHSO$_2$R$^8$ were prepared by methods analogous to those of Example 20:

| Ex | $R^4$ | $R^8$ | M Pt (°C.) |
|---|---|---|---|
| 21 | Ph | Et | 136–138 |
| 22 | Ph | i-Pr | 103–104 |
| 23 | Ph | —N(Me)$_2$ | 100–103 |
| 24 | Ph | n-Pr | 115–117 |
| 25 | Ph | —CH(Me) CO$_2$M3 | |
| 26 | 3-FPh | Me | |
| 27 | 3-FPh | i-Pr | |
| 28 | Ph | cyclopropyl | |
| 29 | 3-FPh | Et | |
| 30 | 3-FPh | —N(Me)$_2$ | |

Example 31

2-(4,6-Dimethoxypyrimidin-2-yl)-N-methanesulfonyl-2methoxy-2-phenylacetamide

2-Chloro-2-(4,6-dimethoxypyrimidin-2-yl)-N-methanesulfonyl-2-phenylacetamide (0.7 g) was boiled under reflux with sodium methoxide (0.2 g) in methanol (30 ml) for 5 hours. The methanol was evaporated off under vacuum. The residue was treated with ether and the precipitated sodium salt was taken into water. The aqueous solution was washed with ether, fresh ether was added, and the whole was acidified with hydrochloric acid. A white solid crystallised from the ether layer. This was filtered off, washed with water and a little ether, and dried to give 0.47 g of the desired product, mp 155°–7° C.

Example 32

2-Acetoxy-2-(4,6-dimethoxypyrimidin-2-yl)-N-methanesulfony-2-phenylacetamide

2-Chloro-2-(4,6-dimethoxypyrimidin-2-yl)-N-methanesulfonyl-2-phenylacetamide (0.5 g) and anhydrous sodium acetate (0.25 g) were refluxed in glacial acetic acid (10 ml) for 7 hours. The acetic acid was evaporated off under vacuum, and the residue was taken into ether. The ether solution was washed with water (3 times), dried over magnesium sulfate, and evaporated under vacuum to give 0.52 g of a brown glass. Trituration with diisopropyl ether gave an off-white solid, which was filtered off, washed with diisopropyl ether and dried to give 0.3 g of the desired product, mp 141°–143° C.

HERBICIDAL EXAMPLE A (Pre-Emergence)

Seeds of the test species listed below were each sown in 8.5 cm square pots filled to within 2 cm of the top with sterile loam, and were covered with a 2–5 mm layer of loam. The pots were watered, and then treated by application to the soil surface in a spray cabinet with the compounds of the Examples listed below formulated as a solution/suspension in 3:1 by volume of acetone and the wetting agent polyoxyethylene (20 mols) monolaurate solution (10 g per litre). The concentration of each test compound and volume of application were calculated to give the desired rate of application of the compound in 200 litres per hectare.

After 3 to 4 weeks growth in a glasshouse (minimum temperature 16° C. for temperate species, 21° C. for non-temperate species, 16 hours per day photoperiod) the plants were visually assessed for any herbicidal response. All differences from an untreated control were scored accordingly to an index where 0=no effect, 1=1–24% effect, 2=25–69% effect, 3=70–89% effect and 4=90–100% effect. In the table below, the following letters are used to denote the plant species:

a—*Triticum aestivum* (wheat)
b—*Hordeum vulgare* (barley)
c—*Beta vulgaris* (sugar beet)
d—*Brassica napus* (rape)
e—*Alopecurus myosuroides* (blackgrass)
f—*Avena fatua* (wild oat)
g—*Agropyron repens* (couch)
h—*Bromus sterilis* (barren brome)
i—*Viola arvensis* (field pansy)
j—*Stellaria media* (chickweed)
k—*Galium aparine* (cleavers)
l—*Matricaria inodora* (scentless mayweed)
m—*Polygonum lapathifolium* (Pale persicaria)
n—*Veronica persica* (Buxbaum's speedwell).

The results obtained were as follows:

| Ex | Kg/ha | a | b | c | d | e | f | g | h | i | j | k | l | m | n |
|----|-------|---|---|---|---|---|---|---|---|---|---|---|---|---|---|
| 2  | 0.25  | 2 | 2 | 3 | 3 | 2 | 3 | 2 | 3 | 4 | 4 | 3 | 0 | 3 | 4 |
| 4  | 1.0   | 2 | 2 | 4 | 2 | 3 | 3 | 3 | 3 | 3 | 4 | 4 | 0 | 3 | 4 |
| 20 | 0.125 | 2 | 2 | 4 | 4 | 3 | 4 | 4 | 3 | 4 | 4 | 4 | 4 | 4 | 4 |

HERBICIDAL EXAMPLE B (Post-Emergence)

The plant species listed below were grown in 8.5 cm square pots containing sterile loam in a glasshouse (minimum temperature 16° C. for temperate species, 21° C. for non-temperate species, 16 hours per day photoperiod), and were treated in a spray cabinet at the 2–3 leaf stage with the compounds of the Examples listed below formulated as a solution/suspension in 1:1 by volume of acetone and the wetting agent polyoxyethylene (20 mols) monolaurate solution (2 g per litre). The concentration of each test compound and volume of application were calculated to give the desired rate of application of the compound in 200 litres per hectare.

After 3–4 weeks, the plants were visually assessed for any herbicidal response. All differences from an untreated control were scored according to an index where 0=no effect, 1=1–24% effect, 2=25–69% effect 3=70–89% effect and 4=90–100% effect.

In the results below, the letters used denote the same plant species as in Herbicidal Example A:

| Ex | Kg/ha | a | b | c | d | e | f | g | h | i | j | k | l | m | n |
|----|-------|---|---|---|---|---|---|---|---|---|---|---|---|---|---|
| 2  | 0.25  | 3 | 2 | 4 |   | 3 | 4 | 3 | 3 | 3 | 4 | 4 | 1 | 3 | 4 |
| 4  | 0.5   | 2 | 2 | 4 | 3 | 3 | 4 | 3 | 2 | 3 | 3 | 4 | 1 | 2 | 3 |
| 8  | 0.25  | 1 | 1 | 3 | 3 | 0 | 2 | 0 | 0 | 2 | 3 | 3 | 0 | 3 | 2 |
| 19 | 0.125 | 1 | 1 | 4 | 2 | 3 | 3 | 2 | 2 | 3 | 3 | 3 | 2 | 2 | 3 |
| 20 | 0.125 | 2 | 2 | 4 | 4 | 2 | 4 | 2 | 2 | 3 | 4 | 4 | 3 | 4 | 4 |

We claim:
1. A compound of the formula:

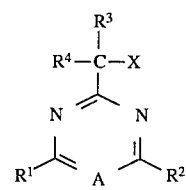

or salts thereof, where:

A is —CH=;

X is —OH, —OR$^{10}$, —SH —SR$^{10}$, —SCN, NH$_2$, or —NHacyl;

R$^1$ and R$^2$, which may be the same or different, each represent alkyl, alkoxy, haloalkyl, haloalkoxy, halo, alkylamino or dialkylamino;

R$^3$ is —CN, —COOR$^5$, —CONR$^6$R$^7$, —CSNH$_2$, —CHO, —CH=Z, —COSR$^{4a}$, —CS$_2$R$^{4a}$, or a substituted or unsubstituted pyridyl or thiophenyl group;

R$^4$ and R$^{4a}$, which may be the same or different, are each H, or a substituted or unsubstituted alkyl, alkenyl, alkynyl, cycloalkyl, phenyl, phenylalkyl, pyridyl or thiophenyl group;

$R^5$ is H, or a substituted or unsubstituted alkyl, alkenyl, alkynyl, cycloalkyl, phenyl, phenylalkyl, pyridyl or thiophenyl group, or a group of the formula:

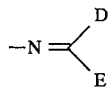

where D and E are each alkyl, or together with the carbon atom to which they are attached form a 5-, 6- or 7-membered carbocyclic ring;

$R^6$ is a group as defined for $R^{4a}$, and $R^7$ is a group as defined for $R^{4a}$ or is $-SO_2R^8$, $-OH$, $-CN$, $-OR^{10}$, $-NH_2$ or $-NHR^{10}$; or $R^6$ and $R^7$ together with the nitrogen atom to which they are attached form a morpholino group;

$R^8$ is a substituted or unsubstituted alkyl, alkenyl, alkynyl, cycloalkyl, aralkyl, phenyl, pyridyl or thiophenyl group, or a group $-NR^{4b}R^{4c}$ where $R^{4b}$ and $R^{4c}$, which may be the same or different, are each a group as defined for $R^{4a}$, or are linked together to complete a ring;

$R^{10}$ is a substituted or unsubstituted alkyl, alkenyl, alkynyl, cycloalkyl, phenyl, phenylalkyl, pyridyl, thiophenyl or acyl group;

Z is $=NOR^{4a}$ or $=N-NR^{4d}R^{12}$, where $R^{4d}$ is a group as defined for $R^{4a}$, and $R^{12}$ is a group as defined for $R^{4a}$ or is a substituted or unsubstituted acyl group, or said $R^{4a}$ and $R^{12}$ groups are linked together to complete a ring;

any alkyl group present in the molecule, unless otherwise defined, is of 1 to 8 carbon atoms and, if substituted, is substituted by one or more halogen atoms, alkoxy groups of 1 to 4 carbon atoms, hydroxy, nitro, mercapto, amino, substituted amino, cyano, acyl, phenyl, pyridyl or thiophenyl groups, or groups of the formula $-SR^8$ or $-SOR^8$, where $R^8$ represents a substituted or unsubstituted alkyl, alkenyl, alkynyl, cycloalkyl, aralkyl, acyl or amino group;

any alkenyl or alkynyl group present in the molecule is of 2 to 6 carbon atoms and, if substituted, is substituted by halogen;

any cycloalkyl group present in the molecule is of 3 to 7 carbon atoms;

any phenyl group present in the molecule, if substituted, is substituted by one or more halogen atoms, optionally substituted alkyl or alkoxy groups of 1 to 4 carbon atoms, hydroxy, nitro, mercapto, amino, alkyl or dialkyl or phenyl substituted amino, cyano, acyl, optionally substituted phenyl, pyridyl or thiophenyl groups, or groups of the formula $-SR^8$ or $-SOR^8$;

any pyridyl or thiophenyl group present in the molecule, if substituted, is substituted by one or more halogen atoms, nitro groups, amino, alkylamino, dialkylamino or acylamino groups, cyano groups, or alkyl or alkoxy groups of 1 to 4 carbon atoms; and any acyl group present in the molecule is a residue of a carboxylic, sulfonic or phosphorus-containing acid;

and with the proviso that, when R4 is ortho-substituted phenyl, any ortho-substituent thereon is halogen, $-NO_2$, $-OH$, $-OR^{10}$, $-SH$, $-SR^8$, $-SOR^8$, $-SO_2R^8$, $-NH_2$, $-NR^6R^{10}$, substituted or unsubstituted phenyl, pyridyl or thiophenyl.

2. The compound according to claim 1 where X is $-OH$ or a group $-OR^{10}$ where $R^{10}$ is alkyl of 1 to 4 carbon atoms, or alkanoyl of 2 to 5 carbon atoms.

3. The compound according to claim 1 where $R^1$ is chloro, methyl, methoxy, difluoromethoxy or ethoxy.

4. The compound according to any of claim 1 where $R^2$ is methyl, methoxy or difluoromethoxy.

5. The compounds according to any of claim 1 where $R^3$ is a group $-COOR^5$ (where $R^5$ is alkyl of 1 to 4 carbon atoms), or $-CONR^6R^7$ (where $R^6$ is hydrogen and $R^7$ is a group $-SO_2R^8$ where $R^8$ is alkyl of 1 to 4 carbon atoms, or $R^6$ and $R^7$ together with the nitrogen atom to which they are attached form a morpholino ring).

6. The compounds according to any of claim 1 where $R^4$ is an unsubstituted alkyl group or a substituted or unsubstituted phenyl group.

7. The compounds according to claim 6 where $R^4$ is isopropyl, phenyl or 3-fluorophenyl.

8. A herbicidal composition which comprises from 0.01 to 99% by weight of one or more compounds according to claim 7 in association with a suitable carrier and/or surface active agent.

9. A method of combating weeds at a locus infested or liable to be infested therewith which comprises applying to said locus an effective amount of one or more compounds according to any of claim 1.

10. A method according to claim 9 in which the amount applied is from 0.001 to 2 kg/ha.

11. The compounds according to claim 2 where $R^1$ is chloro, methyl, methoxy, difluoromethoxy or ethoxy.

12. The compounds according to claim 11 where $R^2$ is methyl, methoxy or difluoromethoxy.

13. The compounds according to claim 12 where $R^3$ is a group $-COOR^5$ (where $R^5$ is alkyl of 1 to 4 carbon atoms) or $-CONR^6R^7$ (where $R^6$ is hydrogen and $R^7$ is a group $-SO_2R^8$ where $R^8$ is alkyl of 1 to 4 carbon atoms, or $R^6$ and $R^7$ together with the nitrogen atom to which they are attached form a morpholino ring).

14. The compounds according to claim 13 where $R^4$ is an unsubstituted alkyl group or a substituted or unsubstituted phenyl group.

15. The compounds according to claim 14 where $R^4$ is isopropyl, phenyl or 3-fluorophenyl.

16. The compounds according to claim 15 where A is $-CH_2=$, $R^1$ and $R^2$ are methoxy, $R^3$ is $CO_2CH_3$ or $CONHSO_2CH_3$, $R^4$ is phenyl and X is hydroxy, methoxy $SH_4$ or $NH_2$.

17. The compounds according to claim 16 in which $R^3$ is $CONH_2SO_2CH_3$ and X is OH.

18. A herbicidal composition which comprises from 0.01 to 99% by weight of one or more compounds according to claim 15, in association with a suitable carrier and/or surface active agent.

19. A herbicidal composition which comprises from 0.01 to 99% by weight of one or more compounds according to claim 17, in association with a suitable carrier and/or surface active agent.

20. A method of combating weeds at a locus infested or liable to be infested therewith which comprises applying to said locus an effective amount of one or more compounds according to claim 15.

21. A method of combating weeds at a locus infested or liable to be infested therewith which comprises applying to said locus an effective amount of one or more compounds according to claim 17.

* * * * *